United States Patent
Feng et al.

(10) Patent No.: US 10,726,551 B2
(45) Date of Patent: Jul. 28, 2020

(54) METHOD FOR RECONSTRUCTING JOINED PART SURFACES OF TWO ADJACENT TEETH OF A 3D DIGITAL MODEL OF TEETH

(71) Applicant: Wuxi EA Medical Instruments Technologies Limited, Wuxi (CN)

(72) Inventors: Yang Feng, Shanghai (CN); Xiaolin Liu, Shanghai (CN)

(73) Assignee: Wuxi EA Medical Instruments Technologies Limited (CN)

( * ) Notice: Subject to any disclaimer, the term of this patent is extended or adjusted under 35 U.S.C. 154(b) by 369 days.

(21) Appl. No.: 15/879,278

(22) Filed: Jan. 24, 2018

(65) Prior Publication Data
US 2018/0268545 A1 Sep. 20, 2018

(30) Foreign Application Priority Data
Mar. 14, 2017 (CN) .......................... 2017 1 0149386

(51) Int. Cl.
G06T 7/00 (2017.01)
G06T 17/20 (2006.01)
G06T 7/73 (2017.01)
G06T 7/50 (2017.01)
G16H 40/63 (2018.01)
G16H 50/50 (2018.01)
(Continued)

(52) U.S. Cl.
CPC .............. *G06T 7/0014* (2013.01); *G06T 7/50* (2017.01); *G06T 7/74* (2017.01); *G06T 17/20* (2013.01); *G16H 40/63* (2018.01); *G16H 50/50* (2018.01); *A61B 5/1072* (2013.01); *A61B 5/1077* (2013.01); *A61B 5/4547* (2013.01); *G06T 2200/04* (2013.01); *G06T 2207/30036* (2013.01); *G06T 2210/41* (2013.01)

(58) Field of Classification Search
CPC ................ A61C 13/0004; A61C 7/002; G06T 2207/30036; G06T 17/00; G06T 17/20
See application file for complete search history.

(56) References Cited

U.S. PATENT DOCUMENTS

2002/0055081 A1\* 5/2002 Hughes ..................... A61C 7/00
433/24
2013/0181983 A1\* 7/2013 Kitamura ................ G06T 17/10
345/419

OTHER PUBLICATIONS

Overdetermined System, Wikipedia: the free encyclopedia, https://en.wikipedia.org/w/index.php?title=Overdetermined_system&oldid=739673949, Sep. 16, 2016 (Year: 2016).\*

(Continued)

*Primary Examiner* — Vincent Rudolph
*Assistant Examiner* — Raphael Schwartz
(74) *Attorney, Agent, or Firm* — Forge IP, PLLC (57) ABSTRACT

A method for reconstructing joined part surfaces of two adjacent teeth of a 3D digital model of teeth is provided. The method includes: obtaining a 3D digital model of teeth which includes adjacent first tooth and second tooth having joined surfaces; identifying a set of intersection points of the joined surfaces; fitting a first plane using the set of intersection points; identifying a set of first control points from points on the 3D digital model of teeth near the set of intersection points basis curvature, where the set of first control points defines boundary of a first part surface of the first tooth to be reconstructed; reconstructing the first part surface using a linear equation system constructed basis the first plane and the set of first control points.

19 Claims, 5 Drawing Sheets

(51) Int. Cl.
*A61B 5/00* (2006.01)
*A61B 5/107* (2006.01)

(56) References Cited

OTHER PUBLICATIONS

Hugues Hoppe, et al, "Surface Reconstruction from Unorganized Points", Computer Graphics, 26, 2, Jul. 1992.
Vaughan Pratt, "Direct Least-Squares Fitting of Alegraic Surfaces", Computer Graphics, vol. 21, No. 4, Jul. 1987.

* cited by examiner

METHOD FOR RECONSTRUCTING JOINED PART SURFACES OF TWO ADJACENT TEETH OF A 3D DIGITAL MODEL OF TEETH

CROSS-REFERENCE TO RELATED APPLICATIONS

This application claims priority from Chinese Patent Application Serial Number 201710149386.6 filed Mar. 14, 2017, which is incorporated herein by reference in its entirety.

FIELD OF THE APPLICATION

The present application is generally related to a method for reconstructing joined part surfaces of adjacent teeth of a three dimensional digital model of teeth.

BACKGROUND

With development of computing technology, it is more and more dependent on computer aided methods in dental area. For instance, in orthodontic area, three dimensional (3D) digital models of teeth are used in many cases. One example is that dental appliances, such as shell shaped retainers and teeth repositioners, can be manufactured basis 3D digital models of jaws.

Most often used methods for obtaining a 3D digital model of a patient's jaw include: scanning a plaster cast fabricated basis a dental impression; scanning a dental impression directly; and scanning the patient's jaw directly. However, due to limited precision of scanning and residual material etc., in a 3D digital model of a jaw obtained by the above methods, surfaces of adjacent teeth may be joined. To utilize a 3D digital model of a jaw, in many cases, it requires to separate teeth from each other. For adjacent teeth that are joined, their joined part surfaces need to be reconstructed after separation, such that shape of a tooth with a reconstructed joined part surface is more similar to the real tooth. Unfortunately, currently effective method for reconstructing joined part surfaces of two adjacent teeth is not available.

SUMMARY

In one aspect, the present application provides a method for reconstructing joined part surfaces of two adjacent teeth of a 3D digital model of teeth. The method includes: obtaining a 3D digital model of teeth which includes adjacent first tooth and second tooth having joined surfaces; identifying a set of intersection points of the joined surfaces; fitting a first plane using the set of intersection points; identifying a set of first control points from points on the 3D digital model of teeth near the set of intersection points basis curvature, where the set of first control points defines boundary of a first part surface of the first tooth to be reconstructed; reconstructing the first part surface using a linear equation system constructed basis the first plane and the set of first control points.

In some embodiments, the reconstructed first part surface is set to protrude along a normal of the first plane toward the second tooth.

In some embodiments, the set of first control points may be identified basis one of principal curvature, Gaussian curvature, subordinate curvature, and mean curvature.

In some embodiments, the set of first control points may be identified according to one of a predetermined curvature threshold and a predetermined curvature changing rate threshold.

In some embodiments, the predetermined curvature threshold and the predetermined curvature changing rate threshold may be determined basis precision of the 3D digital model.

In some embodiments, the predetermined curvature threshold and the predetermined curvature changing rate threshold may be determined basis type of the first tooth.

In some embodiments, the method may further include: sampling on the first plane a first set of nodes; sampling on the first plane a first set of points and moving the first set of points along a normal of the first plane toward the first tooth, to obtain a set of second control points; constructing the linear equation system basis the set of first control points, the set of second control points and the first set of nodes; solving the linear equation system to obtain a first set of Z coordinate values for the first set of nodes if a 3D coordinate system, whose Z axes is parallel with a normal of the first plane, is used; and reconstructing the first part surface basis the first set of nodes with the first set of Z coordinate values.

In some embodiments, the first set of points may be sampled within an area defined by projection of the set of intersection points on the first plane.

In some embodiments, the first set of nodes may be obtained by sampling within a maximum area defined by the greatest and the smallest X and Y coordinate values of projection of the set of intersection points on the first plane.

In some embodiments, the first set of points may be moved by a first predetermined step to obtain the set of second control points.

In some embodiments, the first predetermined step may be calculated by dividing the minimum distance between the set of first control points and the first plane by a first predetermined number.

In some embodiments, the method may further include: if the reconstructed first part surface and a reconstructed second part surface of the second tooth collides with each other, then adjusting Z coordinate values of the set of second control points by a second predetermined step toward the first tooth; constructing a new linear equation system basis the set of first control points, the set of second control points with updated Z coordinate values, and the first set of nodes; solving the linear equation system to obtain a second set of Z coordinate values for the first set of nodes; and reconstructing a new first part surface basis the first set of nodes with the second set of Z coordinate values.

In some embodiments, the second predetermined step may be calculated by dividing the minimum distance between the set of first control points and the first plane by a second predetermined number.

In some embodiments, the method may further include: sampling a second set of points on the first plane within a quadrilateral area defined by projection of two end points of the set of intersection points and projection of two end points of the set of first control points on the first plane, and adjusting Z coordinate values of the second set of points toward the first tooth to obtain a set of third control points, where the linear equation system is constructed basis the set of first control points, the set of second control points, the set of third control points and the set of nodes.

In some embodiments, Z coordinate values of the second set of points may be adjusted by a third predetermined step toward the first tooth.

In some embodiments, the third predetermined step may be calculated by dividing the minimum distance between the set of first control points and the first plane by a third predetermined number.

In some embodiments, the linear equation system may include a first coefficient for controlling the balance between distances from the reconstructed first part surface to the set of second control points and stiffness of the reconstructed first part surface along X axes.

In some embodiments, the linear equation system may include a second coefficient for controlling the balance between distances from the reconstructed first part surface to the set of second control points and stiffness of the reconstructed first part surface along Y axes.

In some embodiments, the linear equation system may be overdetermined linear equation system.

In some embodiments, the first plane may be fitted using a least square method basis the set of the intersection points.

DETAILED DESCRIPTION OF ILLUSTRATED EMBODIMENTS

Figure 1:
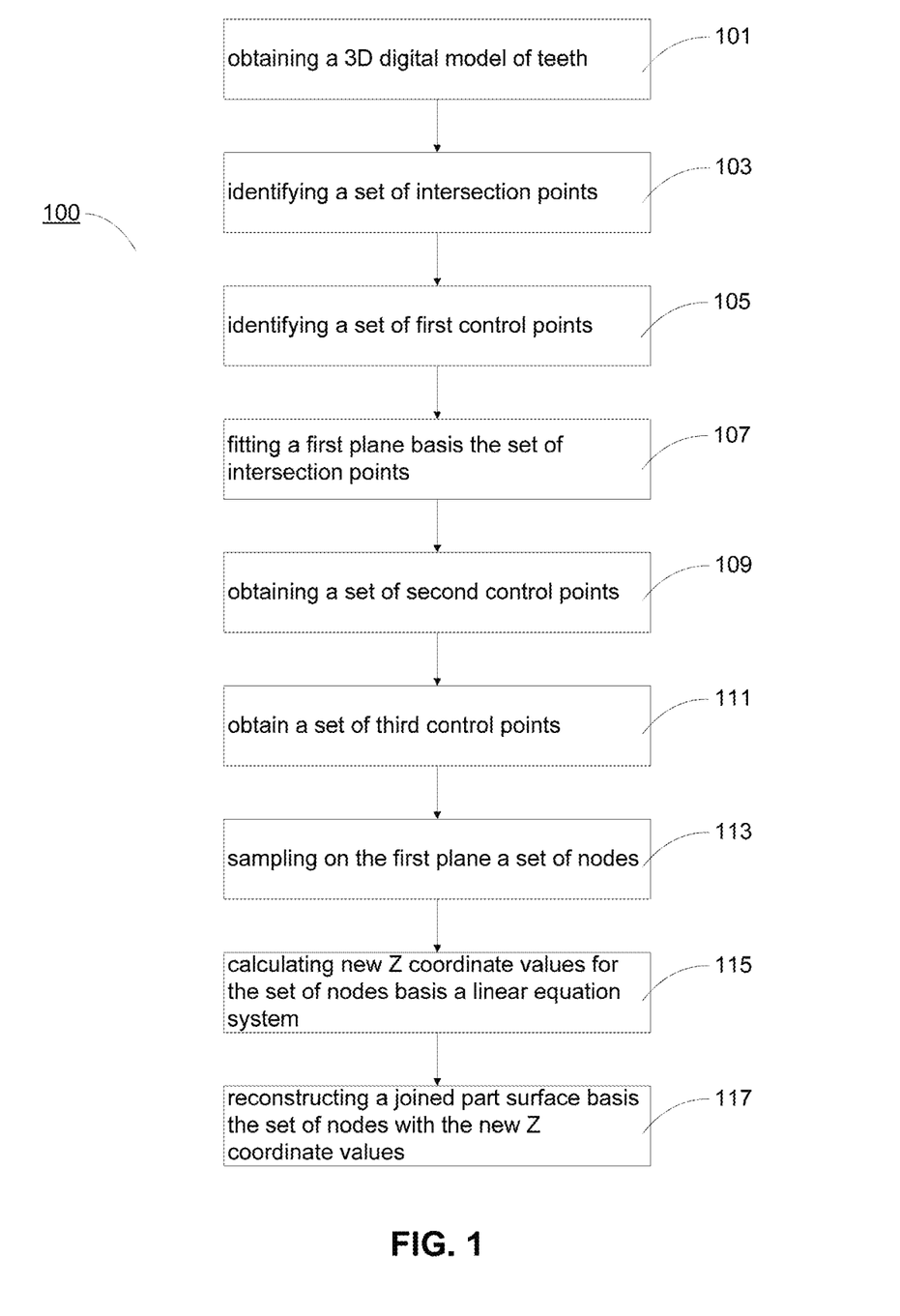
FIG. 1 illustrates a schematic flow chart of a method for reconstructing joined part surfaces of two adjacent teeth of a 3D digital model of teeth according to one embodiment of the present application.

In one aspect, a method for reconstructing joined part surfaces of adjacent teeth of a 3D digital model of teeth is provided. FIG. 1 illustrates a schematic flow chart of a method 100 for reconstructing joined part surfaces of two adjacent teeth of a 3D digital model of teeth according to one embodiment.

In 101, a 3D digital model of teeth is obtained.

In some embodiments, a 3D digital model of teeth may be obtained by scanning a patient's teeth, a teeth model or a dental impression. Due to limited precision of scanning and residual material etc., adjacent teeth in a 3D digital model of teeth obtained by scanning may be joined or collide with each other.

Figure 2A:
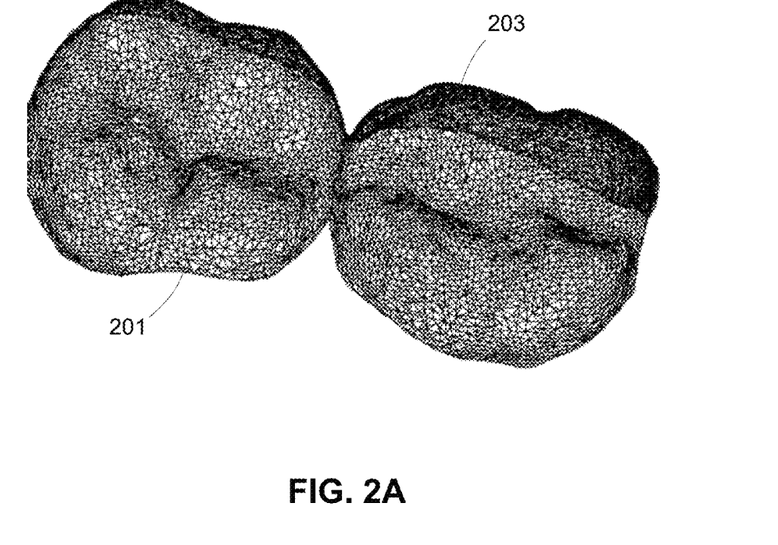
FIG. 2A illustrates two joined teeth of a 3D digital model of teeth according to one embodiment of the present application.

FIG. 2A illustrates a 3D digital model of teeth according to one embodiment.

In this embodiment, the 3D digital model is constructed basis triangular mesh. However, inspired by the present application, one skilled in the art understands that a 3D digital model may also be constructed basis any suitable mesh such as quadrilateral mesh, pentagonal mesh and hexagonal mesh etc.

Referring to FIG. 2A, tooth 201 and tooth 203 are joined. In some cases, to use the 3D digital model of teeth, tooth 201 and tooth 203 need to be separated and their joined part surfaces need to be reconstructed.

In 103, a set of intersection points of two joined teeth is obtained.

In one embodiment, there are at least two joined teeth in the 3D digital model of teeth obtained in 101. To separate the two joined teeth and to reconstruct their joined part surfaces, a set of intersection points of the two joined teeth may be obtained.

Different methods can be used to identify intersection points of two joined teeth. In one embodiment, the "lowest" points may be identified as intersection points. In another embodiment, intersection points may be identified basis curvature. In another embodiment, an intersecting line may be manually selected through user interface of a computer system, and points on the selected intersecting line can be identified as intersection points.

Figure 2B:
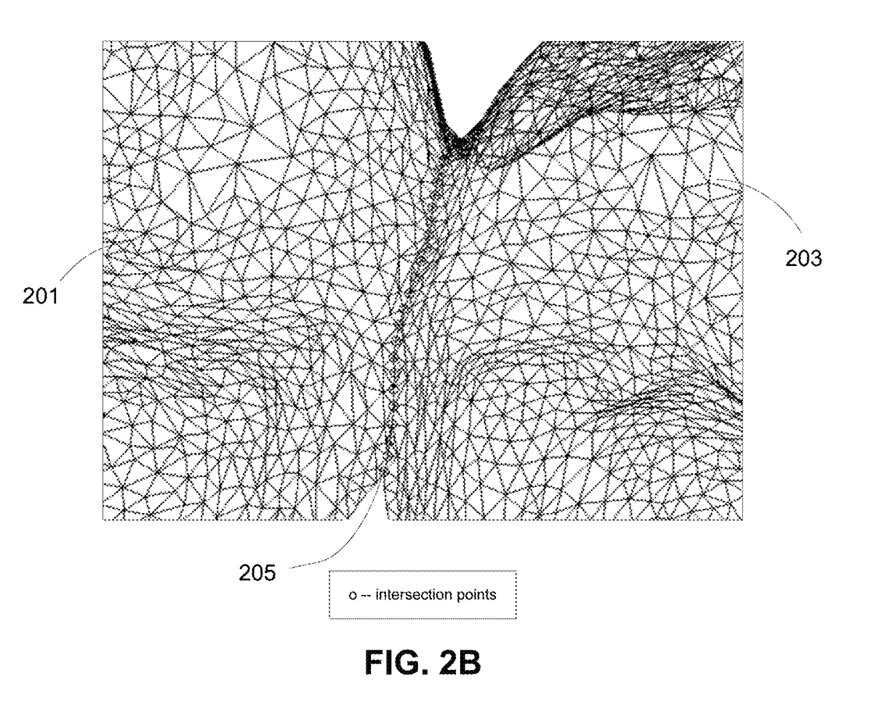
FIG. 2B illustrates identified intersection points of the two joined teeth shown in FIG. 2A.

FIG. 2B illustrates identified intersection points 205 of tooth 201 and tooth 203, where the identified intersection points 205 are marked in circles.

In 105, a set of first control points is identified.

In one embodiment, processes for reconstructing joined part surfaces of tooth 201 and 203 may be similar, therefore below only describes in detail process for reconstructing joined part surface of tooth 201 according to one embodiment.

In one embodiment, curvature calculation may be performed on tooth 201 in an area outside a boundary defined by the set of intersection points, and a set of first control points may be identified according to a predetermined curvature threshold or a predetermined curvature changing rate threshold. The set of first control points defines a boundary of the joined part surface of tooth 201 to be reconstructed.

In some embodiments, if curvature changes fast, then first control points may be identified basis curvature. In one embodiment, if curvature at a point is less than a predetermined curvature threshold, then this point may be identified as a first control point.

In some embodiments, if curvature changing rate changes fast, then first control points may be identified basis curvature changing rate. In one embodiment, if curvature at a point is less than a predetermined curvature changing rate threshold, then this point may be identified as a first control point.

Curvature calculation may be basis principal curvature, Gaussian curvature, subordinate curvature, or mean curvature.

In one embodiment, a curvature threshold or a curvature changing rate threshold may be determined basis scanning precision and/or type of tooth whose joined part surface needs to be reconstructed.

In 107, a first plane is fitted basis the set of intersection points.

In one embodiment, the first plane may be fitted using a least square method basis the set of intersection points. Besides least square methods, there are many other different methods for fitting a plane basis a plurality of points, inspired by the present application, a skilled in the art understands that any other suitable method can be used to fit the first plane, which will not be described in detail here.

In one embodiment, the joined part surfaces of tooth 201 and tooth 203 to be reconstructed may be set to protrude along a normal of the first plane.

In 109, a set of second control points is obtained.

Figure 3:
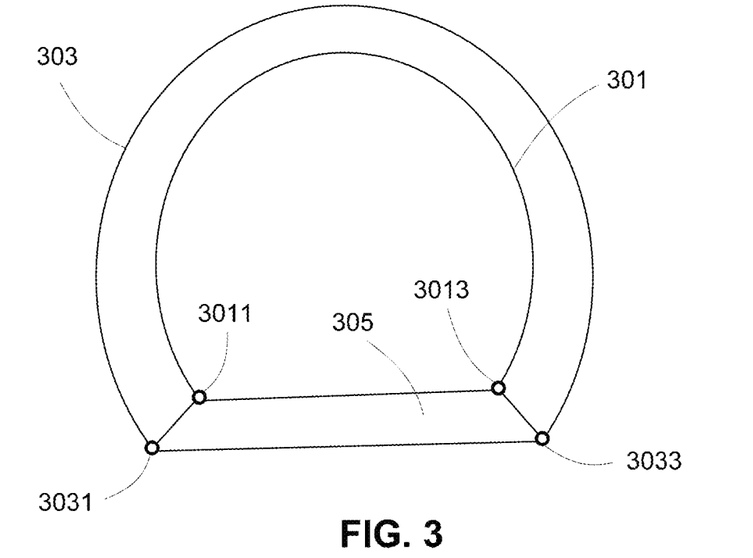
FIG. 3 illustrates areas defined by projection of a set of intersection points and a set of first control points on the first plane according to one embodiment of the present application.

FIG. 3 illustrates areas defined by projection of the set of intersection points and the set of first control points on the first plane according to one embodiment. The projection of the set of intersection points on the first plane defines a boundary 301.

In one embodiment, a first set of points may be sampled on the first plane within an area defined by boundary 301, and the first set of points may be moved along a normal of the first plane toward tooth 201 to obtain the set of second control points.

In one embodiment, a 3D coordinate system, whose Z axes is parallel with a normal of the first plane and X and Y axes are on the first plane, may be used. In this embodiment, the first set of points may be assigned Z coordinate values (toward tooth 201) to obtain the set of second control points.

In one embodiment, the first set of points may be sampled evenly within the area defined by boundary 301. In another embodiment, the first set of points may be sampled within the area defined by boundary 301 according to a predetermined rule, for example, sampling density may change with area.

In one embodiment, the first set of points may be moved along a normal of the first plane by a predetermined step to obtain the set of second control points.

In one embodiment, the predetermined step may be set basis the minimum distance between the set of first control points and the first plane. In one example, the predetermined step may be calculated by dividing the minimum distance by a predetermined number such as one hundred or two hundred etc.

Inspired by the present application, one skilled in the art understands that besides the above examples, there are many other different methods for determining the predetermined step. For example, the predetermined step may be calculated basis the mean distance between the set of first control points and the first plane.

In another embodiment, the first set of points may be moved along a normal of the first plane toward tooth 201 by different distances respectively to obtain the set of second control points. In other words, Z coordinate values of the set of second control points may vary with their X and Y coordinate values.

In 111, a set of third control points is obtained.

In some cases, a joined part of two adjacent teeth may extend to gingiva, and projection of the set of intersection points on the first plane include two end points 3011 and 3013, which are projection of two intersection points of contours of the joined part and gingiva on the first plane. Boundary 301 formed by projection of the set of intersection points on the first plane in such case may be horseshoe shaped.

Similarly, in such case, projection of the set of first control points on the first plane may include two end points 3031 and 3033, and boundary 303 formed by projection of the set of first control points on the first plane may be horseshoe shaped also.

In some embodiments, a second set of points may be sampled within quadrilateral 305 defined by end points 3011, 3013, 3031 and 3033, and the second set of points may be assigned Z coordinate values (moved along a normal of the first plane toward tooth 201) to obtain a set of third control points.

In one embodiment, the second set of points may be sampled within quadrilateral 305 evenly. In another embodiment, the second set of points may be sampled within quadrilateral 305 according to a predetermined rule, for example, sampling density may vary with area.

In one embodiment, to make a part of a reconstructed joined part surface of a tooth, that is close to gingiva, to curve toward the tooth, the second set of points may be moved along a normal of the first plane toward tooth 201 by two steps to obtain the set of third control points. In another embodiment, Z coordinate values of the set of third control points may vary with their X and Y coordinate values.

Figure 4:
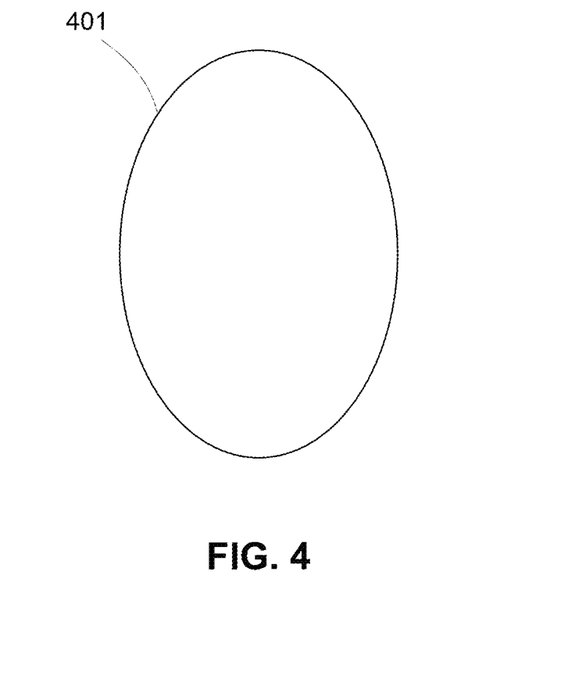
FIG. 4 illustrates an area defined by projection of a set of intersection points on a first plane according to another embodiment of the present application.

FIG. 4 illustrates an area defined by projection of a set of intersection points on the first plane according to one embodiment. In some cases, two adjacent teeth may be joined above gingiva, and projection of the set of intersection points on the first plane forms a boundary 401 which is relatively smooth. In such case, no third control point is needed for reconstructing a joined part surface.

In 113, a set of nodes is sampled on the first plane.

In one embodiment, the set of nodes may be sampled on the first plane within a maximum area defined by maximum and minimum X and Y coordinate values of projection of the set of intersection points on the first plane. In another embodiment, the set of nodes may also be sampled on the first plane within a maximum area defined by maximum and minimum X and Y coordinate values of projection of the set of first control points on the first plane.

In one embodiment, the set of nodes may be sampled evenly. In another embodiment, the set of nodes may be sampled according to a predetermined rule, for example, sampling density of the set of nodes may vary with area.

In one embodiment, number of nodes may be determined according to precision of the joined part surface to be reconstructed, for example, the set of nodes may include 10000 nodes.

The sampled set of nodes have no Z coordinate value, in other words, their Z coordinate values equal to zero. To reconstruct a joined part surface, Z coordinate values of the set of nodes are needed, and in one embodiment, Z coordinate values may be obtained by solving a linear equation system.

In 115, Z coordinate values of the set of nodes are calculated basis a linear equation system.

In one embodiment, a linear equation system may be constructed basis the set of first control points, the set of second control points, the set of third control points and the set of nodes, and Z coordinate values of the set of nodes can be obtained by solving the linear equation system, where the set of first control points defines the boundary of the joined part surface to be reconstructed, the set of second control points controls the shape of a part of the reconstructed joined part surface that is apart from gingiva, and the set of third control points controls the shape of a part of the reconstructed joined part surface that is close to gingiva.

In one embodiment, the linear equation system may be overdetermined linear equation system.

In one embodiment, the linear equation system may be written as:

$$\begin{cases} a_{11}x_1 + a_{12}x_2 + \ldots + a_{1n}x_n = b_1 \\ a_{21}x_1 + a_{22}x_2 + \ldots + a_{2n}x_n = b_2 \\ \ldots \\ a_{m1}x_1 + a_{m2}x_2 + \ldots + a_{mn}x_n = b_m \end{cases} \quad \text{Equation System (1)}$$

The above Equation System (1) may be simplified as:

$$AX = B \quad \text{Equation (1)}$$

wherein, matrix X stands for Z coordinate values of the set of nodes, $$A = \begin{bmatrix} a_{11} & \cdots & +a_{1n} \\ \vdots & \ddots & \vdots \\ a_{m1} & \cdots & +a_{mn} \end{bmatrix} \quad \text{Matrix (1)}$$

$$B = \begin{bmatrix} b_1 \\ \vdots \\ b_m \end{bmatrix} \quad \text{Matrix (2)}$$

In one embodiment, least-square solutions of X may be obtained by orthogonal triangular decomposition of the matrices.

In one embodiment, the first N lines of Matrix A may be for controlling Z coordinate values of the set of nodes, to make them as close to Z coordinate values of control points as possible, where N stands for number of control points which include the set of first control points, the set of second control points and the set of third control points.

The rest 2M lines of Matrix A may be for controlling continuity between the nodes such that derivatives along X and Y axes equal to zero, where M stands for number of nodes.

The first N lines of Matrix B may be Z coordinate values of control points, and the rest lines of Matrix B may be zero.

In one embodiment, bi-linear interpolation algorithm may be used, and in a line of Matrix A corresponding to a control point, only four nodes around the control point have weights, the rest equal to zero.

Therefore, Matrix A may be rewritten as:

$$A \begin{cases} A1 \\ A2 \\ A3 \end{cases} \quad \text{Matrix (3)}$$

wherein, Matrix A1 may be control point constraint, which controls nodes to make them as close to corresponding control points as possible, where Matrix A1 may be written as:

$$A1 = \begin{bmatrix} a1 & b1 & \cdots & c1 & d1 & \cdots & \cdots & \cdots & \cdots \\ \cdots & a2 & b2 & \cdots & c2 & d2 & \cdots & \cdots & \cdots \\ \cdots & \cdots & a3 & b3 & \cdots & c3 & d3 & \cdots & \cdots \\ \cdots & \cdots & \cdots & \ddots & \ddots & \cdots & \ddots & \ddots & \cdots \\ \cdots & \cdots & \cdots & \cdots & aN & bN & \cdots & cN & dN \end{bmatrix} \quad \text{Matrix (4)}$$

wherein, a, b, c and d stand for bi-linear interpolation parameters.

Matrix A2 may be stiffness constraint along X axes, which may be written as:

$$A2 = \begin{bmatrix} e1 & e2 & e3 & \cdots & \cdots & \cdots & \cdots \\ \cdots & e1 & e2 & e3 & \cdots & \cdots & \cdots \\ \cdots & \cdots & e1 & e2 & e3 & \cdots & \cdots \\ \cdots & \cdots & \cdots & \ddots & \ddots & \cdots & \cdots \\ \cdots & \cdots & \cdots & \cdots & e1 & e2 & e3 \end{bmatrix} * S_X \quad \text{Matrix (5)}$$

wherein, $S_x$ stands for coefficient of stiffness along X axes, which is a weight of stiffness of a reconstructed joined part surface, it controls balance between distances from the reconstructed joined part surface to control points and stiffness of the reconstructed joined part surface. In one embodiment, the greater $S_x$, the smoother the reconstructed joined part surface; the less $S_x$, the closer the reconstructed joined part surface to the control points.

In one embodiment, $S_x$ may be determined according to types of adjacent teeth whose joined part surfaces are to be reconstructed. For example, for reconstruction of joined part surfaces of adjacent anterior teeth, $S_x$ may be set to 10; for reconstruction of joined part surfaces of adjacent lateral anterior tooth and cuspid tooth, $S_x$ may be set to 12.5; for reconstruction of joined part surfaces of adjacent premolar and molar, $S_x$ may be set to 15.

wherein, e1, e2 and e3 are second-order partial derivative coefficients, in one embodiment, they can be set to −1, 2 and −1 respectively.

Matrix A3 may be stiffness constraint along Y axes, which may be written as:

$$A3 = \begin{bmatrix} e1 & \cdots & e2 & \cdots & e3 & \cdots & \cdots & \cdots & \cdots \\ \cdots & e1 & \cdots & e2 & \cdots & e3 & \cdots & \cdots & \cdots \\ \cdots & \cdots & \ddots & \cdots & \ddots & \cdots & \ddots & \cdots & \cdots \\ \cdots & \cdots & \cdots & \ddots & \cdots & \ddots & \cdots & \ddots & \cdots \\ \cdots & \cdots & \cdots & \cdots & e1 & \cdots & e2 & \cdots & e3 \end{bmatrix} * S_Y \quad \text{Matrix (6)}$$

wherein, $S_Y$ stands for coefficient of rigidity along Y axes, which is a weight of stiffness of a reconstructed joined part surface, it controls balance between distances from the reconstructed joined part surface to control points and stiffness of the reconstructed joined part surface. In one embodiment, the greater $S_Y$, the smoother the reconstructed joined part surface; the less $S_Y$, the closer the reconstructed joined part surface to the control points.

In one embodiment, $S_Y$ may be determined according to types of adjacent teeth whose joined part surfaces are to be reconstructed. For example, for reconstruction of joined part surfaces of adjacent anterior teeth, $S_Y$ may be set to 10; for reconstruction of joined part surfaces of adjacent lateral anterior tooth and cuspid tooth, $S_Y$ may be set to 12.5; for reconstruction of joined part surfaces of adjacent premolar and molar, $S_Y$ may be set to 15.

Matrix B may be rewritten as:

$$B \begin{cases} B1 \\ B2 \end{cases} \quad \text{Matrix (7)}$$

wherein, B1 may be rewritten as:

$$B1 = \begin{bmatrix} z1 \\ z2 \\ z3 \\ \vdots \\ zN \end{bmatrix} \quad \text{Matrix (8)}$$

and B2 may be rewritten as:

$$B2 = \begin{bmatrix} 0 \\ 0 \\ 0 \\ \vdots \\ 0 \end{bmatrix} \quad \text{Matrix (9)}$$

New Z coordinate values of the set of nodes may be calculated basis the above linear equation system.

Based on the above, one skilled in the art can understand that the set of second control points is for controlling shape of a part of the joined part surface which is close to dental crown of tooth 201, and the set of third control points is for controlling shape of the rest part of the joined part surface which is close to gingiva.

In 117, a joined part surface is reconstructed basis the set of nodes with the new Z coordinate values.

In one embodiment, the reconstructed joined part surface may be formed by the set of nodes with the new Z coordinate values directly.

In another embodiment, the reconstructed joined part surface may be fitted basis the set of nodes with the new Z coordinate values, in other words, besides the set of nodes with the new Z coordinate values, a second set of nodes may be generated basis the set of nodes with the new Z coordinate values, and the reconstructed joined part surface is formed by the set of nodes with the new Z coordinate values and the second set of nodes. In one embodiment, the second set of nodes may be generated using a suitable interpolation algorithm.

In one embodiment, the reconstructed joined part surface may be sutured with tooth 201 at the boundary defined by the set of first control points.

In one embodiment, relaxation process and/or smoothing process may be applied to the suture zone to perfect it.

Figure 5:
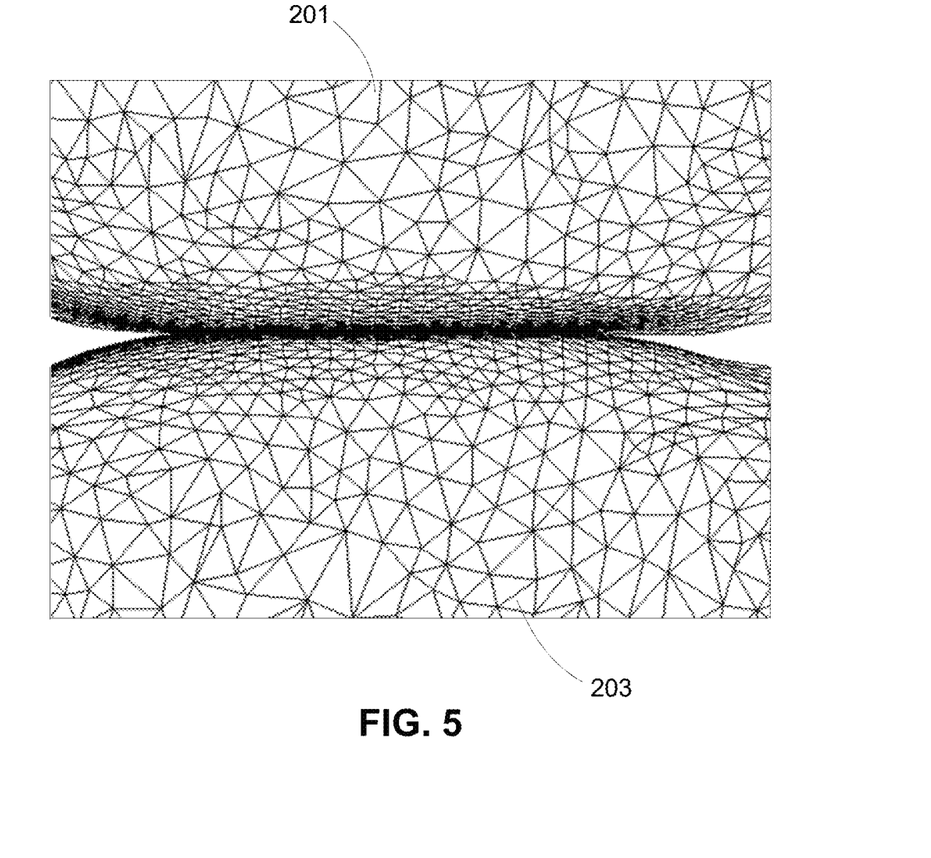
FIG. 5 illustrates the two teeth shown in FIG. 2A with reconstructed joined part surfaces according to one embodiment of the present application.

FIG. 5 illustrates teeth 201 and 203 with reconstructed joined part surfaces which are reconstructed using method 100.

Inspired by the present application, a skilled in the art understands that the present application is not limited to the above surface reconstructing method, any suitable method basis a linear equation system may be used, more examples please refer to "Surface Reconstruction from Unorganized Points" by Hugues Hoppe etc. published on Computer Graphics, 26, 2, Jul. 1992, "Direct Least-Squares Fitting of Algebraic Surfaces" by Vaughan Pratt published on Computer Graphics, Volume 21, Number 4, Jul. 1987 etc.

In one embodiment, after joined part surfaces of two adjacent teeth are reconstructed, it can be detected whether the gap between the joined part surfaces is proper, for example, whether the gap is within a predetermined range, or whether the gap is greater than a predetermined distance. Take tooth 201 as example, if the result of the detection is "no", then Z coordinate values of the set of second control points and the set of third control points may be adjusted, and a new joined part surface of tooth 201 may be reconstructed basis the set of second control points and the set of third control points with adjusted Z coordinate values. For example, if the gap is too small, or if there is collision between the reconstructed joined part surfaces, then Z coordinate values of the set of second control points and the set of third control points may be adjusted toward tooth 201, vice versa.

Inspired by the present application, a skilled in the art understands that to adjust the gap between reconstructed joined part surfaces of two adjacent teeth, a new joined part surface may be reconstructed for at least one of the two adjacent teeth.

Figure 6:
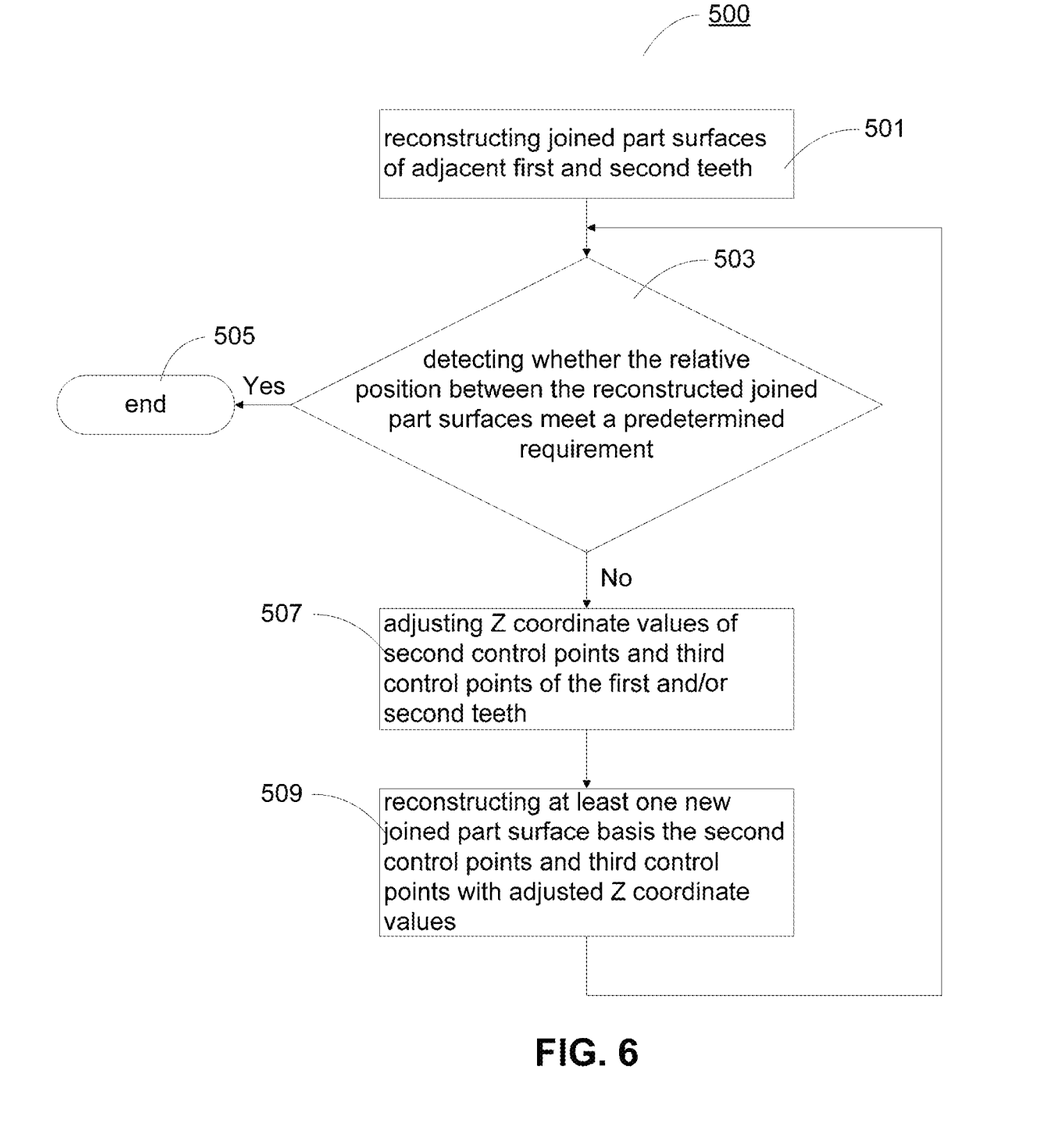
FIG. 6 illustrates a schematic flow chart of a method for reconstructing joined part surfaces of two adjacent teeth of a 3D digital model of teeth according to one embodiment of the present application.

FIG. 6 illustrates a schematic flow chart of a method 500 for reconstructing joined part surfaces of two adjacent teeth.

In 501, joined part surfaces of adjacent first tooth and second tooth are reconstructed.

In one embodiment, the joined part surfaces may be reconstructed using the above method 100.

In 503, it is detected whether the relative position between the reconstructed joined part surfaces meet a predetermined requirement.

In one embodiment, the predetermined requirement may be that there is no collision between the reconstructed joined part surfaces. In another embodiment, the predetermined requirement may be that the gap between the reconstructed joined part surfaces is greater than a predetermined threshold.

If the reconstructed joined part surfaces meet the predetermined non-collision requirement, then jump to 505, method 500 ends.

If the reconstructed joined part surfaces do not meet the predetermined non-collision requirement, then corresponding parameters may be adjusted, and new joined part surfaces may be reconstructed basis the adjusted parameters.

In 507, Z coordinate values of the set of second control points and the set of third control points are adjusted.

If there is collision between the reconstructed joined part surfaces of tooth 201 and tooth 203, or the gap between the reconstructed joined part surfaces of tooth 201 and tooth 203 is less than a predetermined distance, then Z coordinate values of the set of second control points and the set of third control points may be adjusted toward tooth 201, for example, by one step.

In 509, a new joined part surface is reconstructed basis the set of second control points and the set of third control points with adjusted Z coordinate values.

After the new joined part surface is reconstructed, it jumps to 503, to detect whether current reconstructed joined part surfaces meet the predetermined non-collision requirement. 503, 507 and 509 may be repeated until joined part surfaces of tooth 201 and tooth 203, whose gap meet the predetermined requirement, are reconstructed.

Inspired by the present application, a skilled in the art understands that a same position may be defined by a position relative to a reference or by coordinate values in a coordinate system. For example, distance from a first point to a plane equals the Z coordinate value of the first point when a 3D coordinate system, whose X and Y axes are on the plane and Z axes points to the side where the first point locates, is used. Therefore, how a position is defined shall not limit the scope of the present application.

While various embodiments of the disclosed method and apparatus have been described above, it should be understood that they have been presented by way of example only, and not of limitation. Likewise, the various diagrams may depict an example architectural or other configuration for the disclosed method and apparatus, which is done to aid in understanding the features and functionality that can be included in the disclosed method and apparatus. The claimed invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the disclosed method and apparatus. Also, a multitude of different constituent module names other than those depicted herein can be applied to the various partitions. Additionally, with regard to flow diagrams, operational descriptions and method claims, the order in which the blocks are presented herein shall not mandate that various embodiments be implemented to perform the recited functionality in the same order unless the context dictates otherwise.

Although the disclosed method and apparatus is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed method and apparatus, whether or not such embodiments are described and whether or not such features are presented as being a part of a described embodiment. Thus, the breadth and scope of the claimed invention should not be limited by any of the above-described embodiments which are presented as mere examples for illustration only.

We claim:

1. A method for reconstructing joined part surfaces of two adjacent teeth of a 3D digital model of teeth, the method comprising:
    obtaining a 3D digital model of teeth which includes adjacent first tooth and second tooth having joined surfaces;
    identifying a set of intersection points of the joined surfaces;
    fitting a first plane using the set of intersection points;
    identifying a set of first control points from points near the set of intersection points based on curvature, where the set of first control points defines a boundary of a first part surface of the first tooth to be reconstructed;
    sampling on the first plane to obtain a first set of nodes;
    sampling on the first plane a first set of points, and moving the first set of points along a normal of the first plane toward the first tooth, to obtain a set of second control points;
    constructing a linear equation system based on the set of first control points, the set of second control points and the first set of nodes;
    solving the linear equation system to obtain a first set of Z coordinate values for the first set of nodes when a 3D coordinate system, whose Z axis is parallel with a normal of the first plane, is used; and
    reconstructing the first part surface based on the first set of nodes with the first set of Z coordinate values.

2. The method of claim 1, wherein the reconstructed first part surface is set to protrude along a normal of the first plane toward the second tooth.

3. The method of claim 1, wherein the set of first control points is identified based on one of principal curvature, Gaussian curvature, subordinate curvature, and mean curvature.

4. The method of claim 1, wherein the set of first control points is identified according to one of a predetermined curvature threshold and a predetermined curvature changing rate threshold.

5. The method of claim 4, wherein the predetermined curvature threshold and the predetermined curvature changing rate threshold are determined based on precision of the 3D digital model.

6. The method of claim 4, wherein the predetermined curvature threshold and the predetermined curvature changing rate threshold are determined based on type of the first tooth.

7. The method of claim 1, wherein the first set of point is sampled within an area defined by projection of the set of intersection points on the first plane.

8. The method of claim 1, wherein the first set of nodes is sampled within a maximum area defined by the greatest and the smallest X and Y coordinate values of projection of the set of intersection points on the first plane.

9. The method of claim 1, wherein the first set of points is moved by a first predetermined step to obtain the set of second control points.

10. The method of claim 9, wherein the first predetermined step is calculated by dividing the minimum distance between the set of first control points and the first plane by a first predetermined number.

11. The method of claim 1 further comprising:
    if the reconstructed first part surface and a reconstructed second part surface of the second tooth collides with each other, adjusting Z coordinate values of the set of second control points by a second predetermined step toward the first tooth;
    constructing a new linear equation system based on the set of first control points, the set of second control points with updated Z coordinate values, and the first set of nodes;
    solving the new linear equation system to obtain a second set of Z coordinate values for the first set of nodes; and
    reconstructing a new first part surface based on the first set of nodes with the second set of Z coordinate values.

12. The method of claim 11, wherein the second predetermined step is calculated by dividing the minimum distance between the set of first control points and the first plane by a second predetermined number.

13. The method of claim 1, further comprising: sampling a second set of points on the first plane within a quadrilateral area defined by projection of two end points of the set of intersection points and projection of two end points of the set of first control points on the first plane, and adjusting Z coordinate values of the second set of points toward the first tooth to obtain a set of third control points, where the linear equation system is constructed based on the set of first control points, the set of second control points, the set of third control points and the set of nodes.

14. The method of claim 13, wherein the set of third control points is obtained by moving the second set of points along a normal of the first plane toward the first tooth by a third predetermined step.

15. The method of claim 14, wherein, the third predetermined step is calculated by dividing the minimum distance between the set of first control points and the first plane by a third predetermined number.

16. The method of claim 1, wherein the linear equation system includes a first coefficient for controlling balance between (a) distances from the reconstructed first part surface to the set of second control points and (b) stiffness of the reconstructed first part surface, along X axes.

17. The method of claim 1, wherein the linear equation system includes a second coefficient for controlling the balance between (c) distances from the reconstructed first part surface to the set of second control points and (d) stiffness of the reconstructed first part surface, along Y axes.

18. The method of claim 1, wherein the linear equation system is overdetermined linear equation system.

19. The method of claim 1, wherein the first plane is fitted using a least square method based on the set of intersection points.

\* \* \* \* \*